United States Patent
Kalinski et al.

[19]

[11] Patent Number: 5,972,008
[45] Date of Patent: Oct. 26, 1999

[54] METHOD AND APPARATUS FOR RETAINING A SURGICAL MESH

[76] Inventors: Robert J. Kalinski, 1 Hook Dr., Milford, N.J. 08848; Deborah M. Transue, 524 Juniper La., Bridgewater, N.J. 08807

[21] Appl. No.: 09/069,789

[22] Filed: Apr. 29, 1998

[51] Int. Cl.$^6$ ............................ A61B 17/04; A61B 17/06
[52] U.S. Cl. ............................................ 606/151; 206/440
[58] Field of Search .............................. 606/151; 206/440

[56] References Cited

U.S. PATENT DOCUMENTS

| | | | |
|---|---|---|---|
| 2,513,771 | 7/1950 | Williams | 128/335 |
| 3,770,119 | 11/1973 | Hultberg et al. | 206/440 |
| 4,042,109 | 8/1977 | Barcan | 206/440 |
| 4,860,895 | 8/1989 | Iaslovits | 206/426 |
| 5,249,682 | 10/1993 | Transue | 206/438 |
| 5,254,133 | 10/1993 | Seid | 606/215 |
| 5,284,244 | 2/1994 | O'Toole et al. | 206/363 |
| 5,334,217 | 8/1994 | Das | 606/213 |
| 5,540,324 | 7/1996 | Knapp | 206/6.1 |

*Primary Examiner*—Gary Jackson
*Attorney, Agent, or Firm*—Hal Brent Woodrow

[57] ABSTRACT

A retaining apparatus for a surgical mesh includes a top surface and a bottom surface. The top surface has a central elongated recess for receiving a portion of the surgical mesh. Retaining straps are provided for securing the surgical mesh portion to the recess. Centrally located within the recess is an inverted dimple for fitting into a cylindrical opening of the surgical mesh. The inverted dimple restricts lateral movement of the surgical mesh.

19 Claims, 3 Drawing Sheets

METHOD AND APPARATUS FOR RETAINING A SURGICAL MESH

FIELD OF THE INVENTION

The present invention relates generally to the field of surgical devices. More particularly, the present invention relates to a method and apparatus for receiving and retaining a surgical mesh.

BACKGROUND OF THE INVENTION

Surgical meshes are typically employed to repair or obturate a hernia. One surgical mesh device which has proven to be particularly efficacious in the treatment of hernias consists of a cylindrical hernial canal insert terminating at one end with a collar and at the other end with a base. The canal insert is inserted in the hernial canal and extends there through for obturation. The collar and base facilitate fixation of the canal insert and are positioned on the outside and inside surfaces, respectively, of the abdominal cavity adjacent to the hernial cavity.

Conventional techniques for transporting and storing such devices are not entirely satisfactory. These techniques often lead to damage or alteration of the shape of the surgical mesh. The canal insert, typically having a cylindrical shape, is intended to be inserted into a hernial canal of corresponding size and shape. The shape of the device facilitates the insertion and placement of the device for treatment of hernias. If the device is crushed during shipping, it will be difficult for the surgeon to use the device and properly place it in the patient. Moreover, the canal insert is of a size sufficient to allow the insertion of a finger or instrument for purposes of facilitating insertion of the surgical mesh. Therefore, the maintenance of the shape of the surgical mesh device is very important.

However, given the delicate three-dimensional shape of the surgical mesh device, i.e. the collar and base portions of the surgical mesh being typically located some distance away from each other with the canal insert there between, it is difficult to prevent alteration of the device's three-dimensional shape during shipping.

It is therefore an object of the present invention to provide a method and apparatus for retaining a surgical mesh device which ensures that the three dimensional shape of the surgical mesh device is maintained.

It is a further object of the present invention to provide a method and apparatus for retaining a surgical mesh device whereby displacement of the surgical mesh device therefrom is prevented.

It is another object of the present invention to provide a retainer which can easily have a surgical mesh device secured therein.

It is still further object of the present invention to provide a retainer for a surgical mesh device which can be easily manufactured.

These and other objects and advantages of the invention will become more fully apparent from the description and claims which follow or may be learned by the practice of the invention.

SUMMARY OF THE INVENTION

The present invention is directed to a method and apparatus for receiving and retaining a surgical mesh device. The retainer comprises a top surface and a bottom surface. The top surface includes a recess for receiving a portion of the surgical mesh device. At least one strap is provided for retaining the surgical mesh device portion in the recess. Each strap includes at least one attaching device for attaching the strap to the top surface of the retainer. The strap may further include a protrusion which is used to prevent movement of the surgical mesh device portion from within the recess when the strap is attached to the top surface of the retainer. The attaching device, protrusion, and strap may be formed as a unitary structure. An inverted dimple may be provided in the recess. The inverted dimple fits into a cylindrical opening provided in the surgical mesh device. Hence, lateral movement of the surgical mesh device is thereby prevented.

BRIEF DESCRIPTION OF THE DRAWINGS

In order that the manner in which the above-recited and other advantages and objects of the invention are obtained can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

DETAILED DESCRIPTION OF THE PREFERRED EMBODIMENT

Figure 1:
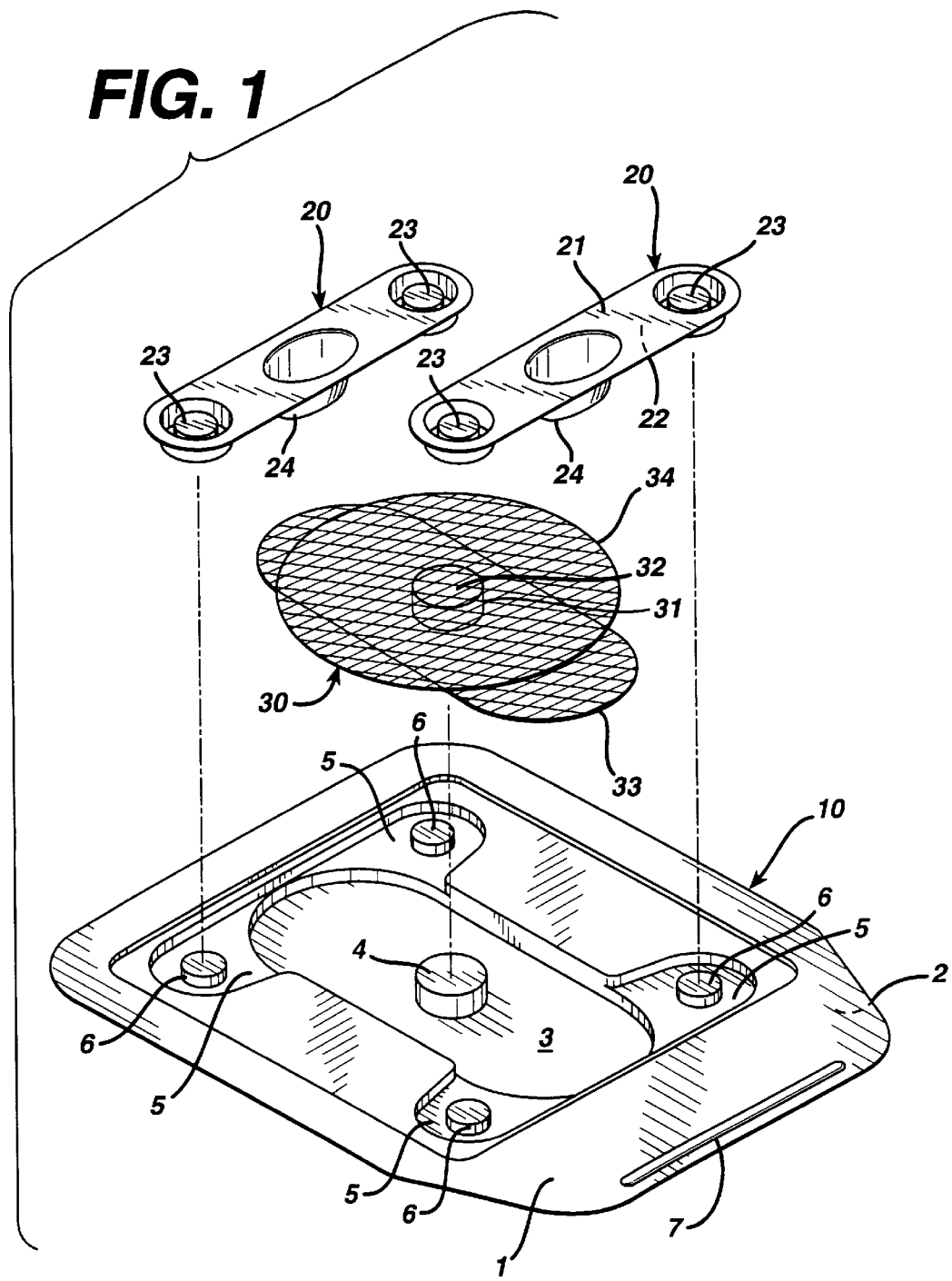
FIG. 1 is an exploded view of a retainer, in accordance with a preferred embodiment of the present invention. A surgical mesh device intended to be retained in the retainer is also shown for purposes of illustration.

Reference will now be made to the drawings wherein like structures are provided with like reference designations. It will be understood that the drawings included herewith only provide diagrammatic representations of the presently preferred structures of the present invention and that structures falling within the scope of the present invention may include structures different than those shown in the drawings.

Figure 2:
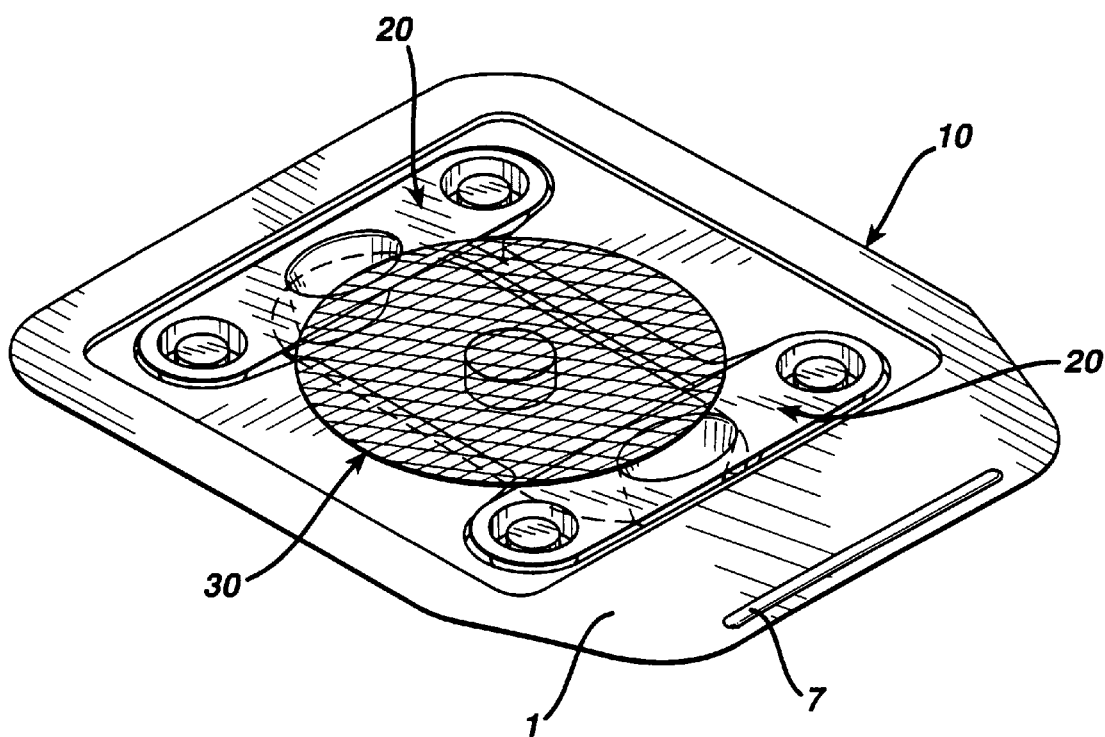
FIG. 2 is an assembled view of the retainer and surgical mesh device shown in FIG. 1.
Figure 3:
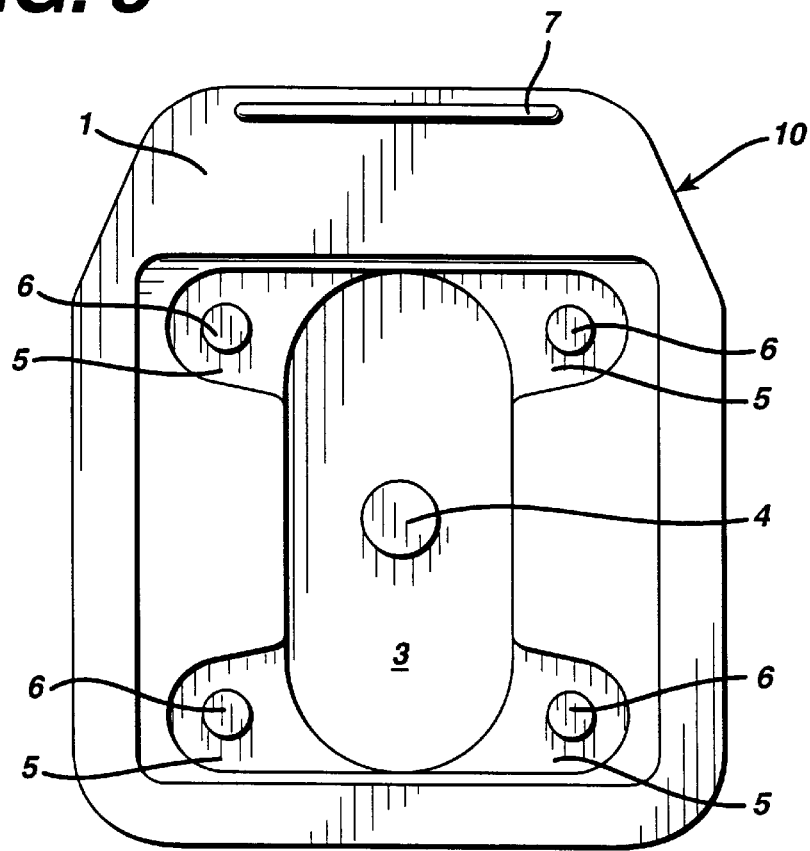
FIG. 3 is a plan view of the retainer shown in FIG. 1.
Figure 4:
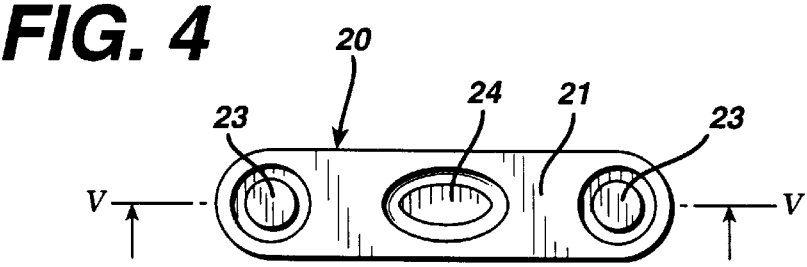
FIG. 4 is a plan view of one strap of the retainer shown in FIG. 1.
Figure 5:
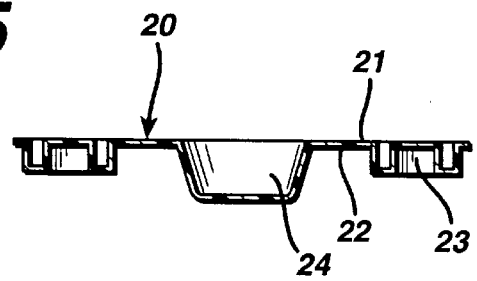
FIG. 5 is a view of the strap taken along the line V—V in FIG. 4.

Referring to FIGS. 1–5 and in particular FIG. 1, there is shown an exploded view of a retainer 10 in accordance with a preferred embodiment of the present invention. A surgical mesh 30 intended to be retained in the retainer 10 is also shown for purposes of illustrating the retainer's function and will therefore be briefly described. A surgical mesh device 30 of a type intended to be retained by the retainer 10 of the present invention is also shown in FIG. 2. The surgical mesh device 30 of this type is to be employed to repair or obturate a hernia. The surgical mesh device 30 includes a cylindrical hernial canal insert 31 terminating at one end with a collar 33 and al: the other end with a base 34. The material of the surgical mesh device 30 is not of particular relevance. However, it is preferably selected to be sufficiently flexible for insertion purposes and biocompatible. The canal insert 31 is inserted in the hernial canal and extends there through for obturation. The collar 33 and base 34 facilitate fixation of the canal insert 31 and are positioned on the outside and inside surfaces, respectively, of the abdominal cavity adjacent the hernial cavity. In this particular embodiment, the collar 33 is elongated.

The retainer 10 is composed preferably of plastic or any other suitable material and comprises a top surface 1 and a bottom surface 2. The top surface 1 includes a recess 3 which is preferably centrally located within the top surface 1. The recess 3 may be formed of any shape as long as it substantially corresponds to the shape of the collar 33 intended to be contained therein. Preferably, the shape of the recess 3 is elongated. An inverted dimple 4 having a circular cross-section is formed within the recess 3.

Two pairs of indentations 5 are located at opposite ends of the recess 3. Each indentation 5 pair has a portion of the recess 3 there between. The depth of the indentations 5 are less than the depth of the recess 3 measured from the top surface 1. Located within each indentation 5 is a protuberance 6.

The perimeter of the retainer 10 is substantially rectangular with two adjacent corners thereof being truncated. A rib 7 is located towards the edge between the truncated corners. The rib 7 extends in a line perpendicular to a central longitudinal axis of the recess 3 and is raised parallel to the same direction as the inverted dimple 4 and protuberances 6. The rib 7 facilitates handling of the retainer 10 during the transporting thereof or during the manufacturing processes when used in conjunction with, for example, a gripping tool.

A pair of removable straps 20, which also may preferably be composed of plastic or any suitable material, are provided at opposite ends of the recess 3 for securement of the collar 33 of the surgical mesh 30 in the recess 3. Each strap 20, being identical to each other and therefore interchangeable, includes an upper face 21 and a lower face 22. The lower face 22 includes a receiver 23 formed integrally at each end thereof Each receiver 23 cooperates with a corresponding protuberance 6 such that attachment of the strap 20 to the top surface 1 is realized (i.e. by a frictional, snap or bonding engagement). The bonding can be accomplished by a chemical, thermal or mechanical means. The lower face 22 additionally includes an integrally formed protrusion 24 extending therefrom between the two receivers 23. The protrusion 24 is centrally located within the strap 20 such that upon engagement of the strap 20 to the top surface 1, the protrusion 24 extends to within the recess 3 such that movement of the collar 33 located within the recess 3 is prevented.

When the collar 33 is placed within recess 3, the inverted dimple 4 extends into a cylindrical opening 32 within the canal insert 31 thereby restricting lateral movement of the surgical mesh 30. Additionally, having the straps, along with the protrusions 24, at opposite ends of the recess 3 with the inverted dimple 4 there between provides for a sufficiently secure configuration, thereby vertical movement of the collar is also restricted. This effect is optimized when the inverted dimple 4 is colinear with the protrusions 24 of the straps 20.

In the process for receiving and retaining the surgical mesh device 30 of a type described in the embodiment above, the collar 33 is first placed within the recess 3. Straps 20 are then attached to the top surface 1 to secure the collar 33 within the recess 3.

Alternatively, the collar 33 may be inserted into the recess 3 subsequent to the straps being attached to the top surface 1. This is accomplished due to the fact that the collar 33 is sufficiently flexible so as to allow the bending thereof under the straps.

Furthermore, it is to be understood that although the present invention has been described with reference to a preferred embodiment, various modifications, known to those skilled in the art, may be made to the structures and process steps presented herein without departing from the spirit and scope of the invention as set forth in the several claims appended hereto. For example, instead of using a receiver arrangement to attach the straps 20 to the top surface 1, other fastening configurations may be substituted therefor, such as hook and latch arrangements. However, it is to be understood that a receiver arrangement is preferable since the receivers 23 and corresponding protuberances 6 are formed integrally with the straps 20 and top surface 1, respectively. A s a result of the reduction of components, simplification of the manufacturing processes is achieved.

Additionally, the apparatus may be sealed with a suitable barrier material which is affixed to top surface 1. Suitable barrier material are well known in the art (i.e. Tyvek™). The barrier material is preferably releasable affixed to the top surface 1 with an adhesive. The apparatus will preferably be serilized, sealed and over wrapped with other packaging materials.

What is claimed is:

1. A retainer for receiving and retaining a surgical mesh, said retainer comprising:

a top surface;

a bottom surface;

said top surface includes a recess for receiving a portion of the surgical mesh device; and at least one strap for securing said portion of the surgical mesh to said recess wherein said recess includes an inverted dimple for fitting into a cylindrical opening of said surgical mesh device, said inverted dimple restricts lateral movement of said surgical mesh.

2. The retainer according to claim 1, wherein said recess is centrally located within said top surface.

3. The retainer according to claim 1, wherein said recess is elongated.

4. The retainer according to claim 1, wherein said inverted dimple is centrally located within said recess.

5. The retainer according to claim 1, wherein each strap includes an upper face and a lower face, said lower face includes at least one attaching device for attaching said strap to said top surface.

6. The retainer according to claim 5, wherein each attaching device is integral with said lower face.

7. The retainer according to claim 5, wherein each attaching device includes a receiver.

8. The retainer according to claim 5, wherein said lower face further includes a protrusion extending therefrom.

9. The retainer according to claim 8, wherein said protrusion is integral with said lower face.

10. The retainer according to claim 8, wherein when each strap is attached to said top surface, said protrusion is located within said recess such that movement of said portion of the surgical mesh located within said recess is prevented.

11. The retainer according to claim 8, wherein said lower face includes two attaching devices.

12. The retainer according to claim 11, wherein each attaching device is located at opposite ends of each strap, said protrusion being located between said two attaching devices.

13. The retainer according to claim 1, wherein there are two straps.

14. The retainer according to claim 13, wherein each strap is located at opposite ends of said recess.

15. A method for receiving and retaining a surgical mesh, comprising the steps of:
 a. providing a retainer having a top surface and bottom surface, said top surface includes a recess for receiving a portion of the surgical mesh wherein said recess includes an inverted dimple for fitting into a cylindrical opening of said surgical mesh device, said inverted dimple restricts lateral movement of said surgical mesh;
 b. placing said portion of said surgical mesh in said recess; and
 c. providing at least one strap for securing said portion of said surgical mesh in said recess.

16. The method of claim 15, wherein the steps are performed in the order: a, b, c.

17. The method of claim 15, wherein the steps are performed in the order: a, c, b.

18. The method of claim 15, wherein said recess is centrally located within said top surface.

19. The method of claim 15, wherein said recess is elongated.

* * * * *